US00PP24699P3

(12) United States Plant Patent
Hart et al.

(10) Patent No.: US PP24,699 P3
(45) Date of Patent: Jul. 29, 2014

(54) PEAR TREE NAMED 'PREMP33'

(50) Latin Name: *Pyrus communis*
Varietal Denomination: PremP33

(76) Inventors: Roy Hart, Motueka (NZ); Lester Raymond Brewer, Motueka (NZ)

( * ) Notice: Subject to any disclaimer, the term of this patent is extended or adjusted under 35 U.S.C. 154(b) by 0 days.

(21) Appl. No.: 13/136,644

(22) Filed: Aug. 4, 2011

(65) Prior Publication Data

US 2013/0125271 P1 May 16, 2013

Related U.S. Application Data

(60) Provisional application No. 61/401,029, filed on Aug. 6, 2010.

(51) Int. Cl.
*A01H 5/00* (2006.01)

(52) U.S. Cl.
USPC ..... Plt./176

(58) Field of Classification Search
USPC ..... Plt./176
See application file for complete search history.

*Primary Examiner* — Howard Locker
(74) *Attorney, Agent, or Firm* — Ballew Law

(57) ABSTRACT

A new and distinct pear tree named 'PremP33' is disclosed. The new pear is notable for its large fruit size, long shelf life and texture.

2 Drawing Sheets

Latin name of the genus and species of the plant claimed: *Pyrus communis.*
Variety denomination: 'PREMP33'.

CROSS-REFERENCE TO RELATED APPLICATIONS

This is a Non-Provisional Plant Patent Application based upon Provisional Patent Application No. 61/401,029 and claims priority under 35 U.S.C. 199(e).

STATEMENT REGARDING FEDERALLY SPONSORED RESEARCH OR DEVELOPMENT

None.

BRIEF DESCRIPTION OF THE PHOTOGRAPHS

Figure 1:
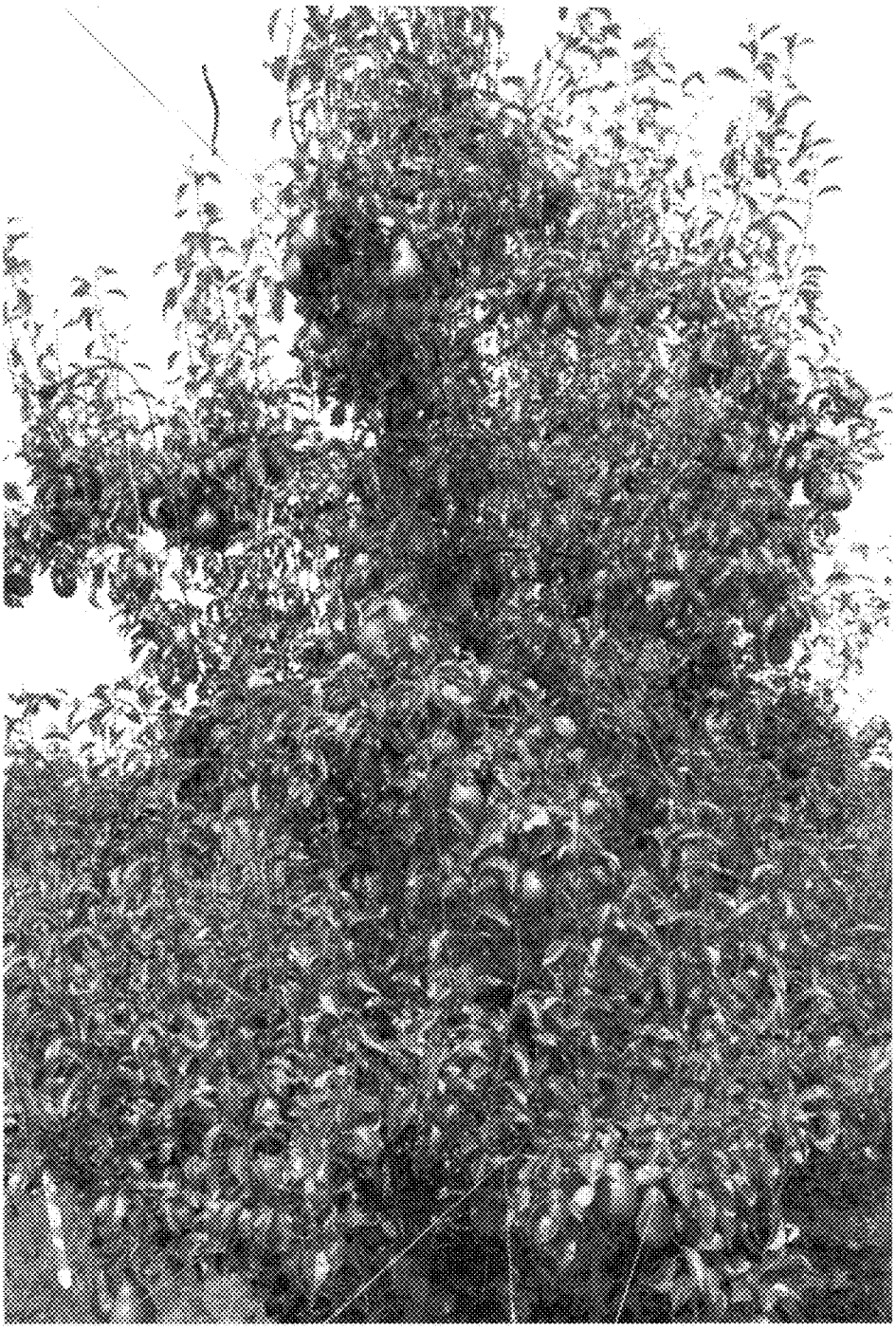
Figure 2:
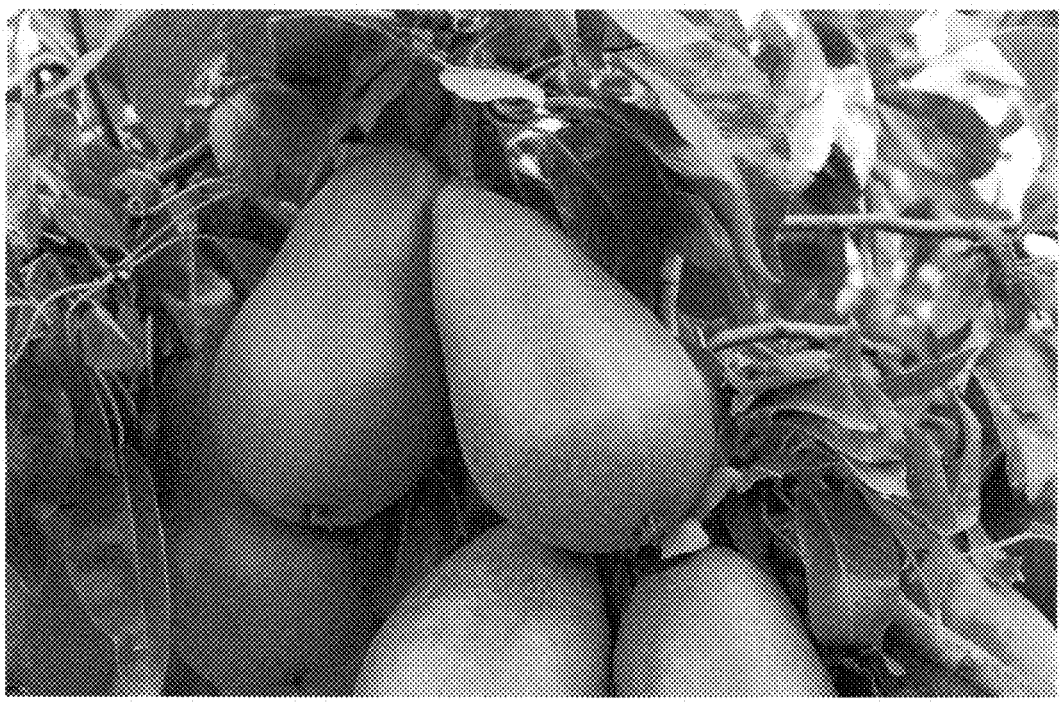

FIG. 1 shows a 'PremP33' pear tree;
FIG. 2 shows the fruit of a 'PremP33' pear tree;

BRIEF DESCRIPTION OF THE VARIETY

The new variety of pear tree 'PremP33' was created in the course of a planned breeding program carried out at The New Zealand Institute for Plant and Food Research, Hawkes Bay, New Zealand. 'PremP33' originated as a result of a controlled cross of 'Patrick Barry' (not patented, seed parent) and 'Conference' (not patented, pollen parent). 'PremP33' was selected as a single plant from among a population of seedlings derived from the parents, and was selected for its large fruit size, long shelf life, buttery texture, fruit shape and early flowering. Asexual propagation by budding was first carried out in Nelson, New Zealand. The variety has since been observed over a number of asexually propagated generations, and has been found to remain true to type.

DETAILED BOTANICAL DESCRIPTION OF THE VARIETY

The following detailed botanical description is based on observations made during the 2010 growing season at Parker, Wash. on 5 year old trees. Fruiting commenced at year 4 of the observed trees. All colors are described according to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor.*—Good.
- *Habit.*—Upright-spreading.
- *Size.*—Height 283 cm, spread 122 cm.
- *Trunk.*—Diameter at 30 cm above graft union 6 cm.
- *Bark texture.*—Smooth.
- *Bark color.*—Under color 166B, over color N200D.
- *Lenticels.*—Diameter — 0.1 cm.
- *Lenticel color.*—164A.

Branch:
- *Size.*—Length 41 cm, diameter 0.8 cm at 1 m above graft union.
- *Crotch angle relative to trunk.*—50°.
- *Branch color.*—166B.
- *Lenticel diameter.*—0.1 cm.
- *Lenticel color.*—164A.
- *Lenticel density.*—18 per square inch.

Dormant one-year-old shoot:
- *Pubescence.*—Absent.
- *Size.*—Diameter 0.7 cm, length 59 cm.
- *Internode length.*—3 cm.
- *Color.*—166B; Internode length — 3 cm.
- *Lenticels.*—Quantity 34 per square inch, color 196C, diameter 0.1 cm.

Flower buds:
- *Quantity per spur.*—2 to 3 clusters.
- *Shape.*—Conical.
- *Size.*—Length 0.6 cm; Diameter 0.8 cm.
- *Color.*—144C.

Flowers:
*Color at balloon stage.*—65A pink for 4-5 days.
*Diameter of open flower.*—2 cm.
*Relative position of petal margin.*—Cupped blossoms, petals not touching.
*Depth.*—1.4 cm.
*Number per cluster.*—8-11 blossoms in a cluster.
Pollinizers: Required.
Petals:
*Number per flower.*—5.
*Shape.*—Oval; Apex rounded; Base slightly pointed.
*Size.*—Length 1.6 cm; Diameter 0.1 cm at base, 0.4 cm at apex, 0.9 cm at widest point.
*Margin.*—Ruffled.
*Color.*—Upper surface N155A; Lower surface N155A.
Pistils:
*Size.*—0.8 cm.
*Color.*—145D.
Anthers:
*Quantity.*—11.
*Size.*—0.1 cm.
*Pollen.*—Produced.
*Color.*—N200A.
Stigma:
*Size.*—Diameter 0.1 cm.
*Color.*—153D.
Style:
*Size.*—Diameter 0.1 cm.
*Color.*—155D.
Ovary:
*Size.*—Diameter 0.3 cm.
*Color.*—145A.
Bloom:
*Date of first bloom.*—April 17$^{th}$ in Parker, Wash.
*Date of full bloom.*—April 22$^{nd}$ in Parker, Wash.
Pedicel:
*Size.*—Length 2.4 cm; Diameter 0.2 cm.
*Color.*—145A.
Sepals:
*Quantity.*—5.
*Size.*—Length 0.7 cm; Diameter 0.2 cm.
*Color.*—145B.

Leaf:
*Attitude in relation to shoot.*—Upward.
*Blade margin.*—Serrated.
*Size.*—Length 7.2 cm, Width 3.9 cm.
*Color.*—Upper surface 144A; Lower surface 144D.
Petiole:
*Size.*—Length 1.5 cm; Diameter 0.1 cm.
*Color.*—145B.
*Attitude in relation to shoot.*—80°.
Petiole:
*Length.*—1.5 cm.
*Diameter.*—0.1 cm.
*Color.*—145B.
Fruit:
*Quantity per cluster.*—2-3.
*Size.*—Length 116 mm; Diameter at widest point 65 mm.
*Aperture of eye.*—18.8 mm.
*Depth of eye.*—7.3 mm.
*Sepal size.*—Length 5.3 mm; Width 3.9 mm.
*Sepal color.*—144A.
*Bloom of skin.*—None.
*Greasiness of skin.*—None.
*Color of skin.*—Solid color 144A with 35% spots of russet color 199A.
*Flesh texture.*—Fine, melting like an avocado.
*Juiciness.*—Juicy, sweet — Brix 14°.
*Flesh color.*—155C.
*Stem color.*—N199B.
*Seeds.*—Quantity per fruit 5; Average weight 85 mg; Length 12 mm; Width 5 mm; Color 166A.
*Disease/pest resistance.*—Susceptible to fire blight.
*Frost resistance.*—Tolerant to cold temperatures down to −10° F.
*Shelf life.*—14+ days on the shelf, following up to 10 weeks of cold storage.
Pruning: Pruning and thinning are needed.
Harvest:
*Harvest date range.*—September 25$^{th}$ through October 15$^{th}$ in Parker, Wash.

The invention claimed is:

1. A new and distinct pear tree substantially as shown and described herein.

* * * * *